United States Patent
Gajji et al.

(10) Patent No.: US 9,939,361 B2
(45) Date of Patent: Apr. 10, 2018

(54) AUTOMATED CALCIMETER SYSTEMS

(71) Applicant: Halliburton Energy Services, Inc., Houston, TX (US)

(72) Inventors: Bhargav Gajji, Cypress, TX (US); Ketan Chimanlal Bhaidasna, Houston, TX (US); Shawn Lynn Broussard, Houston, TX (US); Vyacheslav Chernin, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/315,297

(22) PCT Filed: Sep. 23, 2014

(86) PCT No.: PCT/US2014/056907
§ 371 (c)(1),
(2) Date: Nov. 30, 2016

(87) PCT Pub. No.: WO2016/048276
PCT Pub. Date: Mar. 31, 2016

(65) Prior Publication Data
US 2017/0199109 A1    Jul. 13, 2017

(51) Int. Cl.
*G01N 7/18*       (2006.01)
*G01N 33/24*     (2006.01)
*G01N 33/28*     (2006.01)

(52) U.S. Cl.
CPC ........... *G01N 7/18* (2013.01); *G01N 33/2823* (2013.01); *G01N 33/2835* (2013.01)

(58) Field of Classification Search
CPC ........... G01N 7/18; G01N 33/24; G01N 33/28
(Continued)

(56) References Cited

U.S. PATENT DOCUMENTS 2,296,852 A * 9/1942 Horner ................ E21B 49/005
                                                        436/31
2,373,112 A * 4/1945 Francis ............ G01N 27/4162
                                                        340/632
(Continued)

FOREIGN PATENT DOCUMENTS

CN          201780246      *    3/2011
FR              2920226      *    2/2009
WO    WO 2014/60782      *    4/2014

OTHER PUBLICATIONS

Sherrod, L. A. et al, Soil Science Society of America Journal 2002, 66,299-305.*

(Continued)

*Primary Examiner* — Arlen Soderquist
(74) *Attorney, Agent, or Firm* — Tenley Krueger Tumey L.L.P.

(57) ABSTRACT

Automated calcimeter systems and methods of using the same are described. An automated calcimeter system may comprise a reaction chamber; a pressure sensor coupled to the reaction chamber and configured to measure pressure in the reaction chamber; a pump coupled to the reaction chamber; piping coupled to the pump, wherein the piping is of sufficient length to store a preselected volume of acid; and a processor configured to instruct the pump to deliver the preselected volume of acid to the reaction chamber while also drawing a volume of gas from the reaction chamber, wherein the volume of gas is equivalent to the preselected volume of acid.

20 Claims, 7 Drawing Sheets (58) Field of Classification Search
USPC .................................. 436/29, 31–33, 43
See application file for complete search history.

(56) References Cited

U.S. PATENT DOCUMENTS

| | | | | |
|---|---|---|---|---|
| 2,749,220 | A * | 6/1956 | Rochon | G01N 33/0047 436/139 |
| 3,514,996 | A * | 6/1970 | Coustau | E21B 21/08 73/152.04 |
| 3,801,281 | A * | 4/1974 | Thompson | G01N 33/241 436/133 |
| 5,098,844 | A * | 3/1992 | Royle | G01N 33/24 436/174 |
| 5,958,777 | A * | 9/1999 | Espitalie | G01N 33/241 422/54 |
| 7,666,679 | B2 * | 2/2010 | Herzhaft | E21B 49/00 422/68.1 |
| 2004/0203160 | A1 * | 10/2004 | Herzhaft | E21B 49/00 436/32 |
| 2014/0213517 | A1 | 7/2014 | Fujimoto et al. | |
| 2015/0087071 | A1 * | 3/2015 | Kimour | G01N 7/18 436/25 |

OTHER PUBLICATIONS

International Search Report and Written Opinion for International Application No. PCT/US2014/056907 dated Jun. 5, 2015.

* cited by examiner

AUTOMATED CALCIMETER SYSTEMS

BACKGROUND

Provided are automated calcimeter systems and, more particularly, in some embodiments, automated calcimeter systems and methods for automating the measurement and analysis of specific carbonates present in oil well cores or drill cuttings.

Carbonates may be present in various types of oil well cores or drilled cuttings. Generally, the oil well cores or drilled cuttings may comprise various types of alkaline earth carbonates. These alkaline earth carbonates may include, for example, calcium carbonate ($CaCO_3$, also referred to as "calcite"), magnesium carbonate ($MgCO_3$, also referred to as "dolomite"), and the like. During the lifecycle of a well, carbonates such as calcium and magnesium carbonate may build up in drilling fluids and water treatment processes and cause scaling problems in the tubing and other equipment. Over time, this buildup may reduce or cause a complete loss of production in the well. Until the scale is properly treated, the reduction in or loss of production may continue. Reduction in or loss of production may ultimately affect the economic viability of the well. Therefore, it can be important to determine the type of carbonate and the amount present so that the proper chemical treatment may be applied to reduce carbonate buildup.

Generally, identifying the type and amount of carbonate in oil well cores or drilled cuttings consists of measuring the amounts of various carbonates in samples extracted from oil well cores or dilled cuttings. This process generally comprises having an operator subject the extracted sample to a predetermined amount of acid, such as hydrochloric acid (HCl), in a closed chamber to induce an acid-carbonate reaction where carbon dioxide may be released as a gas. The amount of carbon dioxide gas produced may be measured using a pressure sensor and this measurement may then be compared to a calibration curve created from standardized carbonate samples.

Examples of past techniques for this process include placing a small container of acid inside a reaction chamber containing a sample and then shaking the reaction chamber to begin the acid-carbonate reaction. The chamber may then be added to a calcimeter system to measure and record the pressure while the operator may time the acid-carbonate reaction with a stopwatch. This process and other similar processes have required an operator be present, attentive, and actively engaged in the operation. As such, these processes may rely on operator awareness and skill to perform at least some of the tasks involved including measuring the reagents, adding the reagents, initiating the reaction, timing the reaction, measuring the data, recording the data, analyzing the data, etc. Because of this reliance on the operator, the process may be subject to operator error, for example, an erroneous measurement of acid; should an operator make an error or not be attentive enough to prevent a potential issue from occurring, the wrong chemical treatment could be applied. Should the wrong chemical treatment be used, the carbonate buildup may not be removed and further treatments may be required until an effective chemical treatment is used. Therefore, preventing operator error and determining the type and amount of carbonate in a sample may reduce downtime, cost, waste, and may also increase the operational efficiency of the well.

BRIEF DESCRIPTION OF THE DRAWINGS

These drawings illustrate certain aspects of some of the embodiments of the present invention, and should not be used to limit or define the invention.

DETAILED DESCRIPTION

Provided are automated calcimeter systems and methods for automating the measurement and analysis of specific carbonates present in oil well cores or drill cuttings, or, more particularly, measuring the amount of calcium carbonate and/or magnesium carbonate in samples of alkaline earth carbonates.

The automated calcimeter systems may comprise a reservoir, a pump, and a reaction chamber. The reservoir may store an acid. The pump may pump the acid to the reservoir or the reaction chamber and also may be configured to compensate for pressure fluctuations due to the introduction of the acid to the reaction chamber. The reaction chamber may contain the sample to be analyzed and may contain an acid-carbonate reaction upon addition of the acid to the sample. The methods of determining the amount of a specific carbonate in a sample may include measuring the pressure increase in the reaction chamber due to the release of carbon dioxide from an acid-carbonate reaction and also comparing the time that the pressure increase occurred and the magnitude of the pressure increase with a calibration curve. One of the many potential advantages of the apparatus and methods described herein is that the process may be automated and thus may not rely on operator skill or attentiveness in order to function. An additional advantage is that the calibration protocol may be built in to the automated calcimeter system for frequent calibration and the generated calibration curves may be stored and recalled at any time so that they may be compared to any sample measurements. A further advantage is the reduction in errors due to operator mistake. This in turn may reduce the potential application of an ineffective chemical treatment which may consequently reduce the expense and downtime associated with the well.

Generally, the automated calcimeter system may automate an acid-carbonate and the measurement of a gas released from the reaction. A typical acid-carbonate reaction may yield carbon dioxide, water, and a salt. An example of a typical acid-carbonate reaction is illustrated by equation 1 below:

$$CaCO_3(s) + {}_2HCl(aq) \rightarrow CaCl_2(aq) + CO_2(g) + H_2O(l) \qquad \text{(eq. 1)}$$

The acid-carbonate reaction may be any acid-carbonate reaction, for example, a magnesium carbonate and HCl reaction. The carbon dioxide produced by an acid-carbonate reaction may be measurable using any such tool or technique that measures the change in pressure of a closed system. The disclosed methods and apparatus may comply with the American Society for Testing and Materials (ASTM) standard test method D 4373-84, entitled "Standard Test Method for Calcium Carbonate Content in Soils."

Figure 1A:
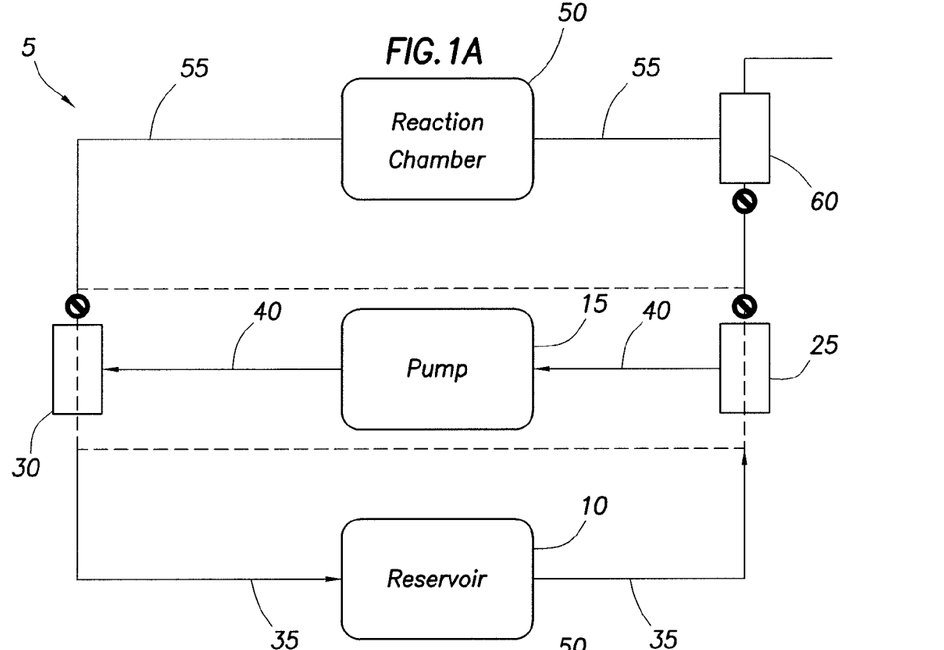
FIG. 1A is a block diagram illustrating an example automated calcimeter system with a closed loop formed between the reservoir and the pump.

FIG. 1A is a block diagram illustrating an example automated calcimeter system 5 with a closed loop formed between reservoir 10 and pump 15. Automated calcimeter system 5 may comprise reservoir 10. Reservoir 10 may be used to contain an acid, for example, HCl. The acid in reservoir 10 may be pumped via pump 15. Pump 15 may be any sort of pump sufficient for use with automated calcimeter system 5. An example of pump 15 is a peristaltic pump. Multiple pumps may also be used in the configuration described by FIG. 1A or in other configurations if desired. Piping connects reservoir 10 and pump 15. The piping connecting reservoir 10 and pump 15 may be separated by valve A 25 and valve B 30. Valve A 25 and valve B 30 may be any type of valve sufficient for use with automated calcimeter system 5. An example valve that may be used for either or both valve A 25 and valve B 30 is a 3/2-way valve which may comprise one common and always open outlet/inlet port, and two directional outlet/inlet ports wherein the outflow/inflow is alternately switched between the two directional outlet/inlet ports. Valve A 25 and valve B 30 may isolate any fluids in automated calcimeter system 5 from any valve operating component and also from the external environment. Valve A 25 and valve B 30 may also separate the piping connecting reservoir 10 and pump 15 into two separate piping sections which are identified as reservoir piping 35 (e.g., piping connected to reservoir 10) and pump piping 40 (i.e. piping connected to pump 15). Reservoir piping 35 and pump piping 40 may be any piping suitable for use with automated calcimeter system 5.

Reservoir 10 may store the acid required for the acid-carbonate reaction. Once the acid is introduced into reservoir 10, the acid may not be exposed to the external environment at any point in the automated acid-carbonate reaction process. As shown in FIG. 1A, valve A 25 may be a 3/2-way valve and may have a common outlet port that is always open, and two directional inlet ports that alternate between open and closed positions. As shown in FIG. 1A, one directional inlet port may be open and the other may be closed as designated by the "prohibition sign" in FIG. 1A. Acid stored in reservoir 10 may be pumped to the open directional inlet port of valve A 25 and then into and through valve A 25 before exiting valve A 25 through the common outlet port. From there the acid may be pumped though pump piping 40 and pump 15 before being circulated to the common inlet port of valve B 30. As shown in FIG. 1A, valve B 30 may also a 3/2-way valve, but may have a common inlet port that is always open, and two directional outlet ports that alternate between open and closed positions. As shown in FIG. 1A, one directional outlet port is open and the other is closed as designated by the "prohibition sign" in FIG. 1A. The acid that was pumped through pump piping 40 and pump 15 to the common inlet port of valve B 30, may then continue to be pumped through valve B 30 before exiting valve B 30 through the open directional outlet port. The acid may then be pumped via reservoir piping 35 back to reservoir 10. As illustrated and described above, when the directional inlet ports of valve A 25 and the directional outlet ports of valve B 30 are in the directional port configuration illustrated by FIG. 1A, the automated calcimeter system 5 creates a closed loop between reservoir 10 and pump 15. This configuration of valve A 25 and valve B 30 may be referred to as the "priming configuration," wherein the priming configuration isolates any reaction chamber from reservoir 10 while reservoir 10 is in fluid communication with pump 15.

Advantageously, the required amount of acid needed for the acid-carbonate reaction may be stored in pump piping 40 prior to initiating the acid-carbonate reaction. This operation may be described as "priming the system" and generally may comprise drawing the required amount of acid from reservoir 10 and storing that amount of acid in a length of pump piping 40. The length and/or inner diameter of pump piping 40 may be measured and implemented such that the volume of acid stored in the length of pump piping 40 may be the exact volume of acid needed for the acid carbonate reaction. This process may be automated by automated calcimeter system 5 such that the operator may not need to determine and then measure the acid volume and also may not need to isolate the required volume of acid for the acid-carbonate reaction. The priming configuration described in FIG. 1A may be used to prime the automated calcimeter system 5 for the acid-carbonate reaction.

Figure 1B:
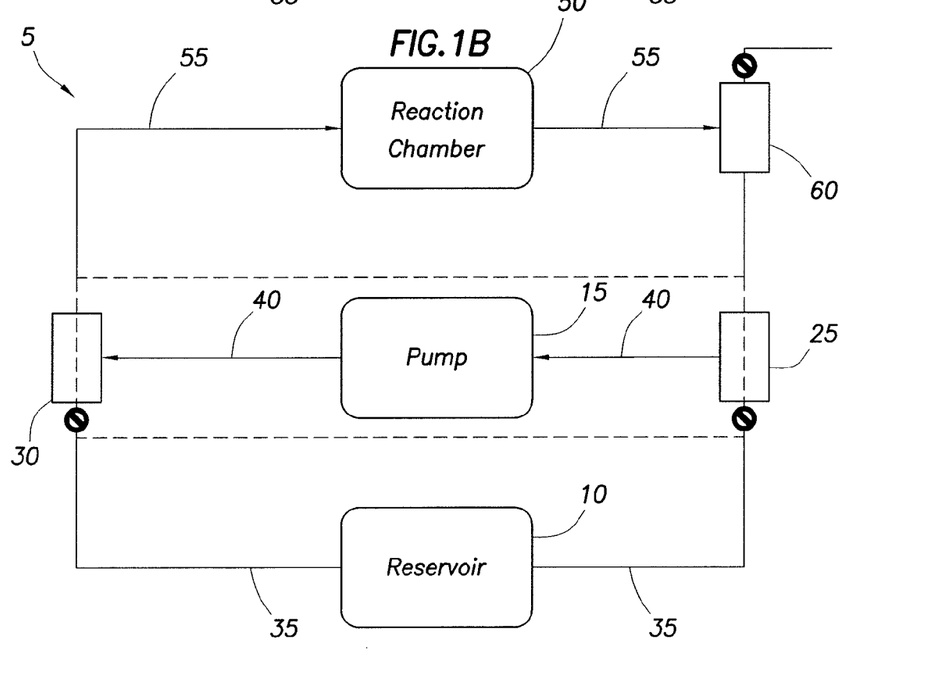
FIG. 1B is a block diagram illustrating an example automated calcimeter system with a closed loop formed between the pump and the reaction chamber.

FIG. 1B is a block diagram illustrating the example automated calcimeter system 5 of FIG. 1A with a closed loop formed between pump 15 and reaction chamber 50. Before the amount of carbonates (e.g., calcium carbonate) in a sample may be determined, the automated calcimeter system 5 may be primed by storing the required amount of acid for the acid-carbonate reaction in pump piping 40 as illustrated by FIG. 1A and described above. After the automated calcimeter system 5 may be primed, the open directional inlet port of valve A 25 connecting reservoir 10 to pump 15 may be closed and the closed directional inlet port of valve A 25 connecting reaction chamber 50 to pump 15 may be opened. Simultaneously or at a different time, the open directional outlet port of valve B 30 connecting pump 15 to reservoir 10 may be closed and the closed directional outlet port of valve B 30 connecting pump 15 to reaction chamber 50 may be opened. This directional port configuration change is noted by the changed position of the prohibition signs in FIG. 1B as compared to FIG. 1A. The opened directional inlet port of valve A 25 and the opened directional outlet port of valve B 30 connect pump 15 and pump piping 40 to reaction chamber 50 via reaction chamber piping 55.

After the automated calcimeter system 5 has been primed, a directional closed outlet port of pressure relief valve 60, which may be located near reaction chamber 50, may be opened to release any pressure in reaction chamber 50 and to obtain a zero pressure reading on the pressure sensor used to measure the pressure change caused by an acid-carbonate reaction. The opened directional outlet port should direct the outflow out of automated calcimeter system 5. After a zero reading is obtained, the opened directional outlet port of pressure relief valve 60 may be closed to secure the internal pressure of automated calcimeter system 5. Pressure relief valve 60 may comprise a 3/2-way valve which comprises one common and always open inlet port, and two directional outlet ports wherein the outflow is alternately switched between the two directional outlet ports. As discussed above one of the directional outlet ports directs the outflow out of automated calcimeter system 5. The other directional outlet port directs the outflow to pump 15.

Acid stored in pump piping 40 may then be pumped by pump 15 to the common inlet port of valve B 30, through valve B 30, and out of valve B 30 via the open directional outlet port. The acid may then be pumped through reaction chamber piping 55 to reaction chamber 50. Reaction chamber 50 may comprise the oil well core or drilled cuttings extracted sample. In reaction chamber 50, the acid may contact the sample and react. The $CO_2$ liberated by an acid-carbonate reaction may be measured by a pressure sensor. The introduction of the acid to reaction chamber 50 should not increase the pressure of reaction chamber 50 because pump 15 pulls an equivalent volume of gas (e.g., air) from reaction chamber 50 as the acid is introduced. Pump 15 may pull an equivalent volume of gas from reaction chamber 50 simultaneously or near simultaneously to the introduction of the acid. This volume of gas may be stored in reaction chamber piping 55 or pump piping 40. As illustrated and described above, when the directional inlet ports of valve A 25 and the directional outlet ports of valve B 30 are in the directional port configuration illustrated by FIG. 1B, the automated calcimeter system 5 may create a closed loop between reaction chamber 50 and pump 15. This configuration of valve A 25 and valve B 30 may be referred to as the "reaction configuration," wherein the reaction configuration isolates reservoir 10 from reaction chamber 50 while reaction chamber 50 is in fluid communication with pump 15. As such, automated calcimeter system 5 may be capable of automated pressure compensation and does not require a separate pressure regulation step or the need of an operator to regulate the internal pressure of automated calcimeter system 5.

The pressure increase in reaction chamber 50 may be recorded as a function of time. Typically, an increase in pressure within the first thirty seconds of the reaction indicates the presence of calcium carbonate. A pressure increase after the first thirty seconds may indicate the presence of another carbonate, for example, magnesium carbonate. When the pressure in reaction chamber 50 reaches a stable value after a designated time, the test may terminate either as programmed or manually by an operator. The pressure increase may then be compared to a calibration curve to determine the content of a specific carbonate in a sample and this information may be displayed and recorded. The closed directional outlet port for pressure relief valve 60 may be opened to release the increased pressure out of automated calcimeter system 5 and reaction chamber 50 may be emptied of its contents. Once the carbonate content has been identified, a treatment specific for the carbonate may be prepared and the treatment may be introduced into the well from which the sample was extracted and used to treat the well.

The samples used for analysis with the automated calcimeter system 5 may be any such samples which may potentially comprise carbonates. Such samples may be alkaline earth carbonate samples extracted from oil well cores or drilled cuttings. Examples of carbonates may include calcium carbonate and magnesium carbonate. Typically, only one gram of sample may be needed for automated calcimeter system 5, however, any amount of sample may be used in accordance with this disclosure. Before use, it is preferable that the sample be dried, free of contaminants, and ground to a size of 100 mesh or finer in order to ensure a sufficient reaction, however these steps may not be necessary. With the benefit of this disclosure, one having ordinary skill in the art should be able to select and prepare an appropriate sample for use with automated calcimeter system 5.

The acid used in the acid-carbonate reaction may be any such acid that may react with a carbonate to produce carbon dioxide. An example of such an acid includes, but should not be limited to, hydrochloric acid. Any volume of acid may be used as well as any concentration or any normality. For example, 10 to 20 mL of 10% [1 normal] HCl may be used to react with one gram of sample. The volume, concentration, and/or normality of the acid may be chosen based on the amount needed to react completely with a predetermined amount of sample. With the benefit of this disclosure, one having ordinary skill in the art should be able to select and prepare an appropriate acid for use with automated calcimeter system 5.

Reservoir 10 may be any such reservoir suitable for storing a volume of acid. Reservoir 10 may be made of any such materials suitable for storing a volume of acid. In automated calcimeter system 5, reservoir 10 may be removable, or alternatively reservoir 10 may comprise an opening in which a volume of acid may be introduced. With the benefit of this disclosure, one having ordinary skill in the art should be able to select an appropriate reservoir for use with automated calcimeter system 5.

Pump 15 may be any such pump suitable for pumping a volume of liquid or gas. Pump 15 may be made of any such materials suitable for pumping a volume of liquid or gas. In automated calcimeter system 5, pump 15 may be removable. Examples of pump 15 may include, but should not be limited to peristaltic pumps. Although a peristaltic pump is described in FIGS. 1A and 1B, any pump that does not cross-contaminate the pumped contents with the pump components or the external environment may be sufficient. With the benefit of this disclosure, one having ordinary skill in the art should be able to select an appropriate pump for use with automated calcimeter system 5. Multiple pumps may be used in any of the configurations described herein or in any other configurations.

Reservoir piping 35, pump piping 40, and reaction chamber piping 55 may be any such piping suitable for transporting and/or storing a volume of liquid or gas. The piping may be made of any such materials suitable for storing a volume of liquid or gas. By way of example, reservoir piping 35, pump piping 40, and reaction chamber piping 35 may be plastic tubing. In automated calcimeter system 5, the piping is may be with reservoir 10, pump 15, valve A 25, valve B 30, reaction chamber 50, and pressure relief valve 60. As discussed above, the length and/or inner diameter of the piping, in particular pump piping 40, should be capable of storing the volume of acid needed for the acid-carbonate reaction so that the automated calcimeter system 5 may be primed prior to initiation of the acid-carbonate reaction. With the benefit of this disclosure, one having ordinary skill in the art should be able to select an appropriate type and length of piping for use with automated calcimeter system 5.

Valve A 25, valve B 30, and pressure relief valve 60 may be any such valve suitable for transporting and directing the inflow/outflow of a volume of liquid or gas. The valves may be made of any such materials suitable for transporting and directing the inflow/outflow of a volume of liquid or gas. In automated calcimeter system 5, the valves are compatible with reservoir 10, pump 15, reservoir piping 35, pump piping 40, reaction chamber 50, and reaction chamber piping 55. The valves may isolate the liquid or gas from the internal valve components and the external environment and are able to direct the inflow/outflow of a volume of a liquid or gas without exposing the volume of liquid or gas to the internal valve components and/or the external environment. Examples of the valves may include, but should not be limited to solenoid valves, check valves, electro-pneumatic valves, electric valves, pneumatic valves, ball valves, diaphragm valves, pinch valves, and the like. Any type of valve configuration suitable for use with the automated calcimeter system 5 may be used. Although a valve configuration described as a 3/2-way configuration is described in FIGS. 1A and 1B, any such valve configuration may be substituted for the 3/2-way valves described in FIGS. 1A and 1B. For example, 1×4-way valves, 2×2-way valves, 4×2-way valves, and the like may also be substituted for any of the 2×3-way valves. Substitution of valves, may allow for different configurations of automated calcimeter system 5. For example, a valve may be used that combines the directional outlet port of pressure relief valve 60 used for relieving pressure in reaction chamber 50 with either valve A 25 or valve B 30, such that the valve may be capable of directing the inflow/outflow of a liquid or gas, and also of relieving the pressure in reaction chamber 50. Such a configuration arrangement in automated calcimeter system 5 may preclude the need for a separate pressure relief valve, such as pressure relief valve 60 as described in FIG. 1B. With the benefit of this disclosure, one having ordinary skill in the art should be able to select an appropriate valve type and configuration for use with automated calcimeter system 5.

Reaction chamber 50 may be any such reaction chamber suitable for containing an acid-carbonate reaction and withstanding the subsequent increase in pressure. Reaction chamber 50 may be made of any such materials suitable for containing an acid-carbonate reaction. In automated calcimeter system 5, reaction chamber 50 may be removable, or alternatively reaction chamber 50 may comprise an opening in which a sample for analysis may be introduced. With the benefit of this disclosure, one having ordinary skill in the art should be able to select an appropriate reaction chamber for use with automated calcimeter system 5.

Reaction chamber 50 may comprise a pressure sensor. The pressure sensor may be made of any such materials suitable for measuring a pressure increase induced by an acid-carbonate reaction. Without limitation, examples of pressure sensors may generally include any such pressure gauges and/or pressure recorders, or more particularly, a bourdon pressure gauge, a piezoresistive strain gauge, capacitive gauge, magnetic gauge, piezoelectric gauge, optical gauge, potentiometric gauge, resonant gauge, pirani (one wire or two wire) gauge, ionization gauge, and the like. In automated calcimeter system 5, the pressure sensor may be attached to a pressure transducer which may convert the pressure measurement to an electric signal that may be registered and interpreted by the electronic components of automated calcimeter system 5, or alternatively the pressure sensor may comprise a pressure transducer. With the benefit of this disclosure, one having ordinary skill in the art should be able to select a pressure sensor for use with automated calcimeter system 5.

The pressure sensor may comprise a pressure gauge and/or pressure recorder and may also comprise a multi-sensor that is capable of measuring the internal temperature of reaction chamber 50. Temperature measurement of reaction chamber 50 at the time of the acid-carbonate reaction may allow for temperature compensation correction in the analysis of the carbonate content calculations, thus, temperature measurement in addition to pressure measurement may potentially provide more accurate measurement of the carbonate content. Alternatively, reaction chamber 50 may comprise a separate temperature measurement sensor that is apart from the pressure sensor. With the benefit of this disclosure, one having ordinary skill in the art should be able to measure the internal temperature of the reaction chamber and compensate for the measurement in the analysis of the carbonate content of a sample.

Figure 2A:
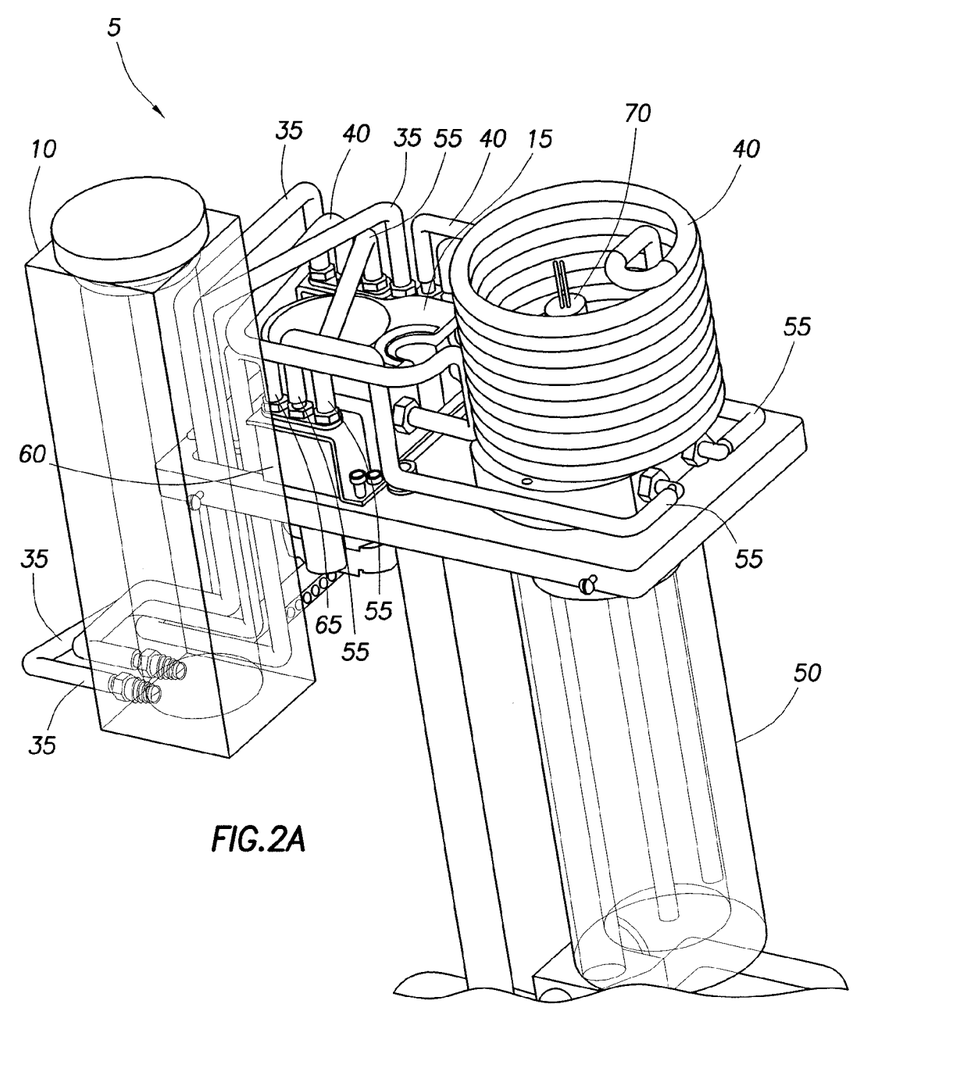
FIG. 2A is an illustration of the internal components of an example automated calcimeter system that may be used for quantifying the amount of carbonates in a sample.

FIG. 2A illustrates one perspective of the internal components of an example automated calcimeter system 5 that may be used for quantifying the amount of carbonates in a sample. As shown in FIG. 2A, reservoir 10 may be connected to pump 15 via reservoir piping 35, valve A 25 (not shown in FIG. 2A), and pump piping 40. Pump 15 may connect to reservoir 10 via pump piping 40, valve B 30 (not shown in FIG. 2A), and reservoir piping 35. Pump 15 may be connected to reaction chamber 50 via pump piping 40, valve B 30 (not shown in FIG. 2A), and reaction chamber piping 55. Reaction chamber 50 may be connected to pump 15 via reaction chamber piping 55, pressure relief valve 60, pump piping 40, and valve A 25 (not shown in FIG. 2A). Additionally, as shown in FIG. 2A and as described above, pressure relief valve 60 may comprise a directional outlet port that directs the outflow out of automated calcimeter system 5. This directional outlet port may be attached to pressure relief piping 65, which is shown extending from pressure relief valve 60 and extending behind reservoir 10. Also as shown in FIG. 2A, is pressure transducer 70. Pressure transducer 70 may convert the pressure readings to an electrical signal that may be registered and interpreted by the electronics of automated calcimeter system 5.

Figure 2B:
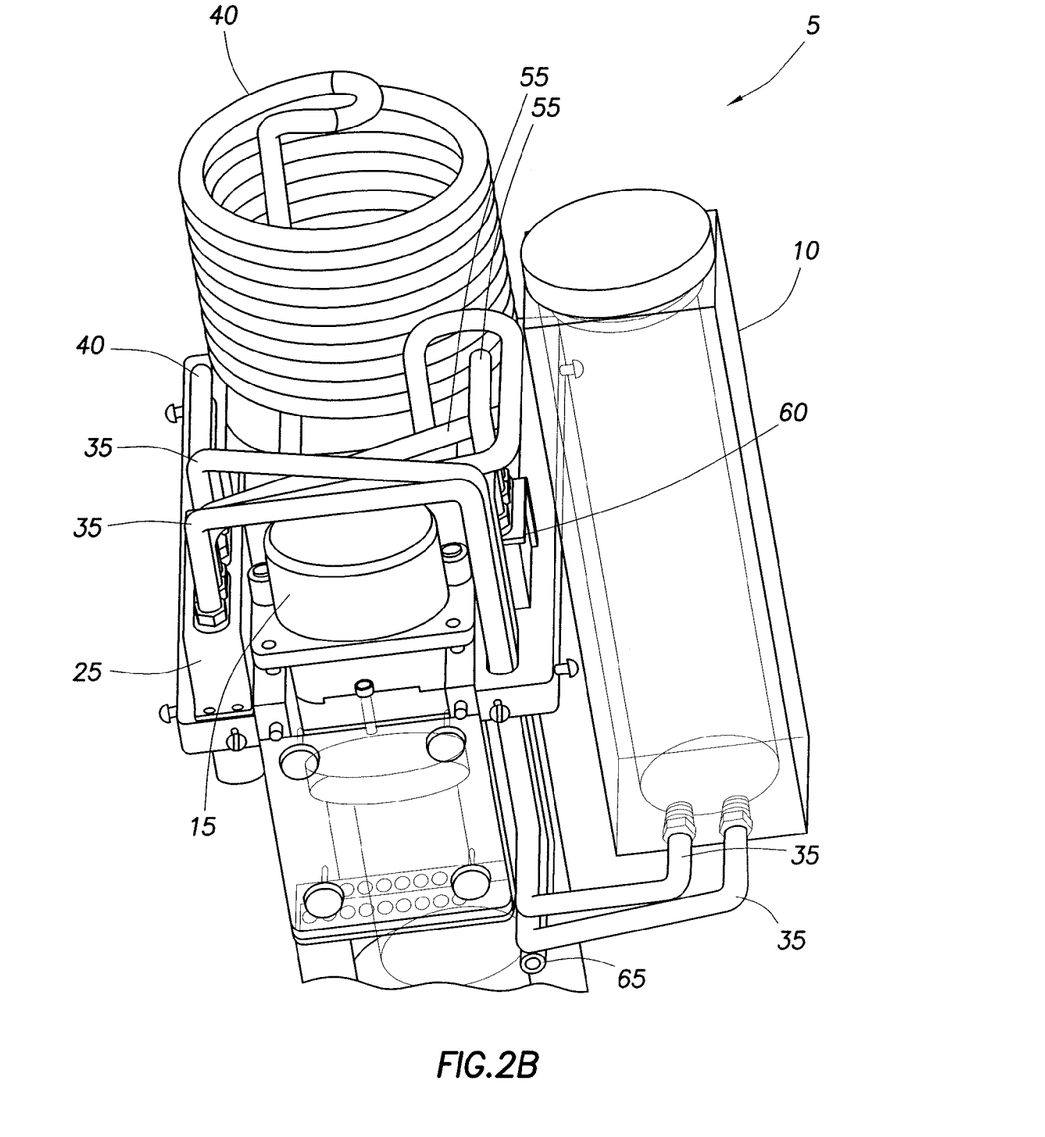
FIG. 2B is an additional illustration of the internal components of an example automated calcimeter system that may be used for quantifying the amount of carbonates in a sample.

FIG. 2B illustrates another perspective of the internal components of the example automated calcimeter system 5 of FIG. 2A. This perspective illustrates the location for valve A 25, which was obscured by reservoir piping 35, pump piping 40, and reaction chamber piping 55 in FIG. 2A. Additionally, FIG. 2B illustrates an exit opening for pressure relief piping 65; the opening was obscured by reservoir 10 in FIG. 2A. The exit opening of pressure relief piping 65 may be used to relieve reaction chamber pressure prior to and subsequent to the acid-carbonate reaction. Pressure relief piping 65 may be left unmodified or may be attached to other piping to suit work site standards.

Figure 2C:
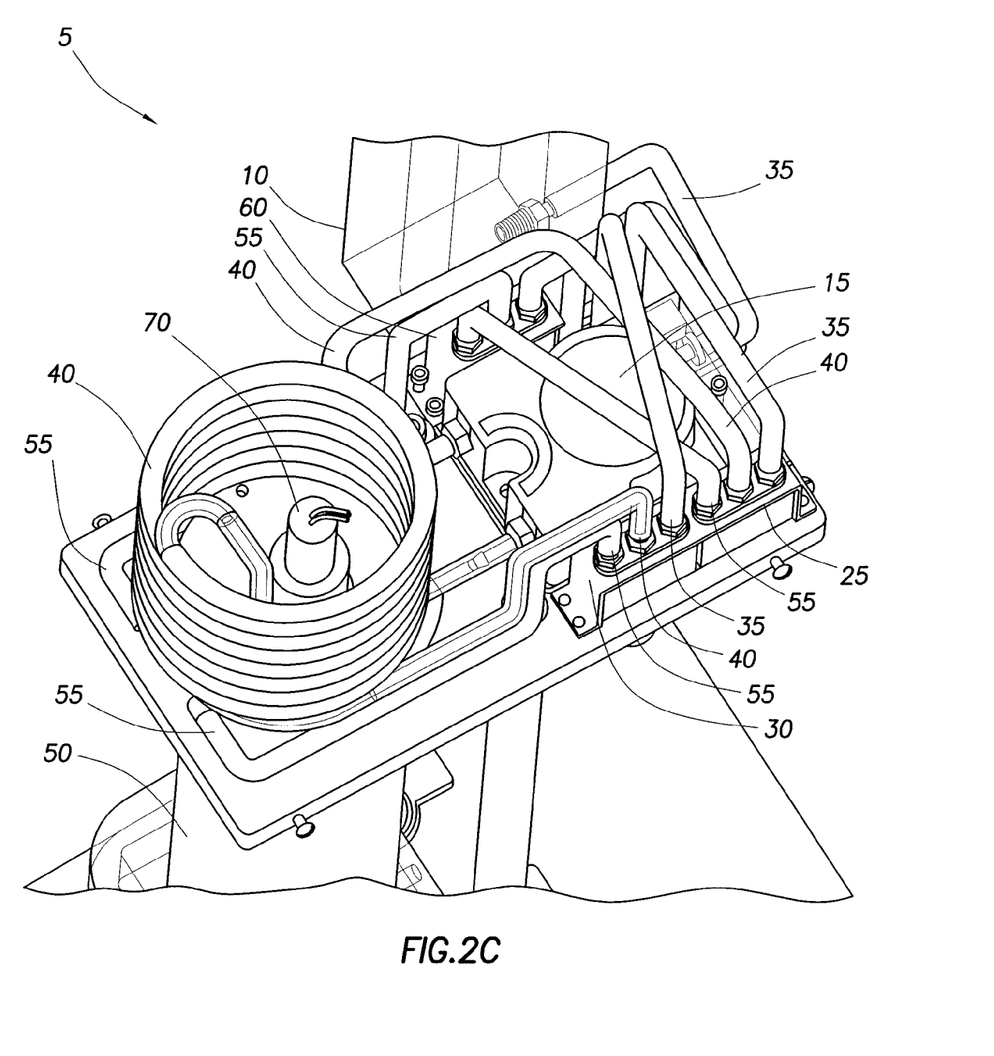
FIG. 2C is an additional illustration of the internal components of an example automated calcimeter system that may be used for quantifying the amount of carbonates in a sample.

FIG. 2C illustrates another perspective of the internal components of the example automated calcimeter system 5 of FIG. 2A. This perspective illustrates a location for valve B 30, which was obscured by reservoir piping 35, pump piping 40, and reaction chamber piping 55 in FIG. 2A; and was obscured by valve A 25 in FIG. 2B. Additionally, FIG. 2C illustrates a top-down perspective for pressure transducer 70.

Figure 3:
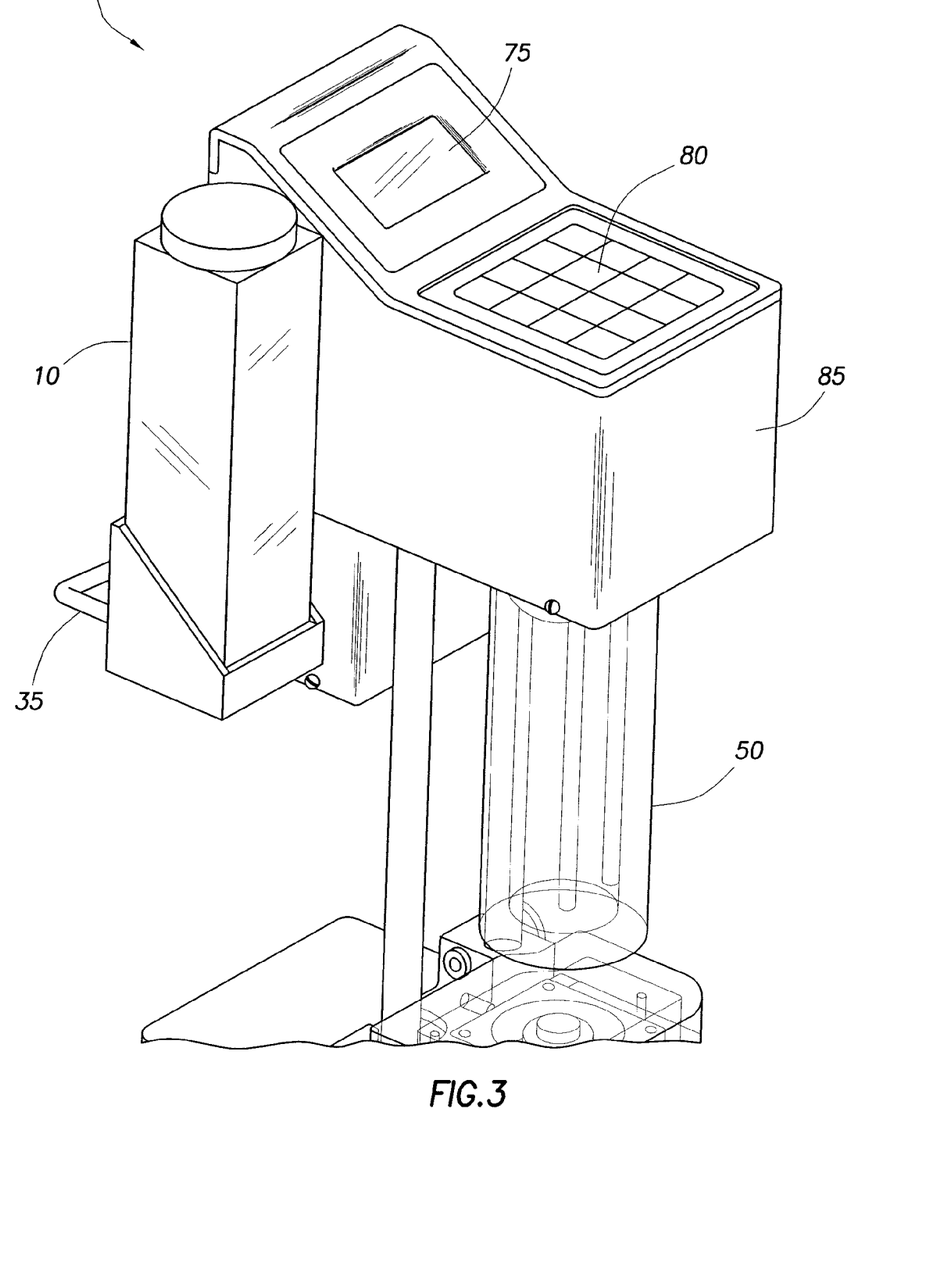
FIG. 3 is an illustration of an example automated calcimeter system comprising an electronics display, control pad, and housing for electronics.

FIG. 3 is an illustration of an example automated calcimeter system 5 comprising an electronics display 75, control pad 80, and electronics housing 85. Additionally, FIG. 3 illustrates reservoir 10 and reaction chamber 50. Electronics display 75 may display input commands and data output. For example, the input commands may comprise any such commands input to automated calcimeter system 5, including start times, sample identification numbers, sample properties (e.g., depth), stop times, desired units of measurement, normality of the acid, etc. Additionally, the display may display a real-time clock and/or timer eliminating the need for an operator to manually time and also manually start and/or stop operation of automated calcimeter system 5. Keypad 80 allows for the input of commands and may comprise a standard or modified key set comprising additional or special characters if desired. Electronic housing 85 may comprise any type of housing suitable for containing the internal electronics of automated calcimeter system 5. The electronics display 75, control pad 80, and internal and/or other components of automated calcimeter system 5 may be used to automate the acid-carbonate reaction and/or the generation of a calibration curve for a specific carbonate. Automated calcimeter system 5 may be programmed to automatically dispense a specified volume of acid from reservoir 10, to prime automated calcimeter system 5, and to react the volume of acid with a sample located in reaction chamber 50. Additionally, the process may be programmed to store, record, and/or analyze alterations in pressure induced by the acid-carbonate reaction. These pressure changes may be measured as a function of time and automated calcimeter system 5 may be programmed to time the acid-carbonate reaction such that any pressure changes induced by the acid-carbonate reaction are correlated with a time measurement.

Figure 4:
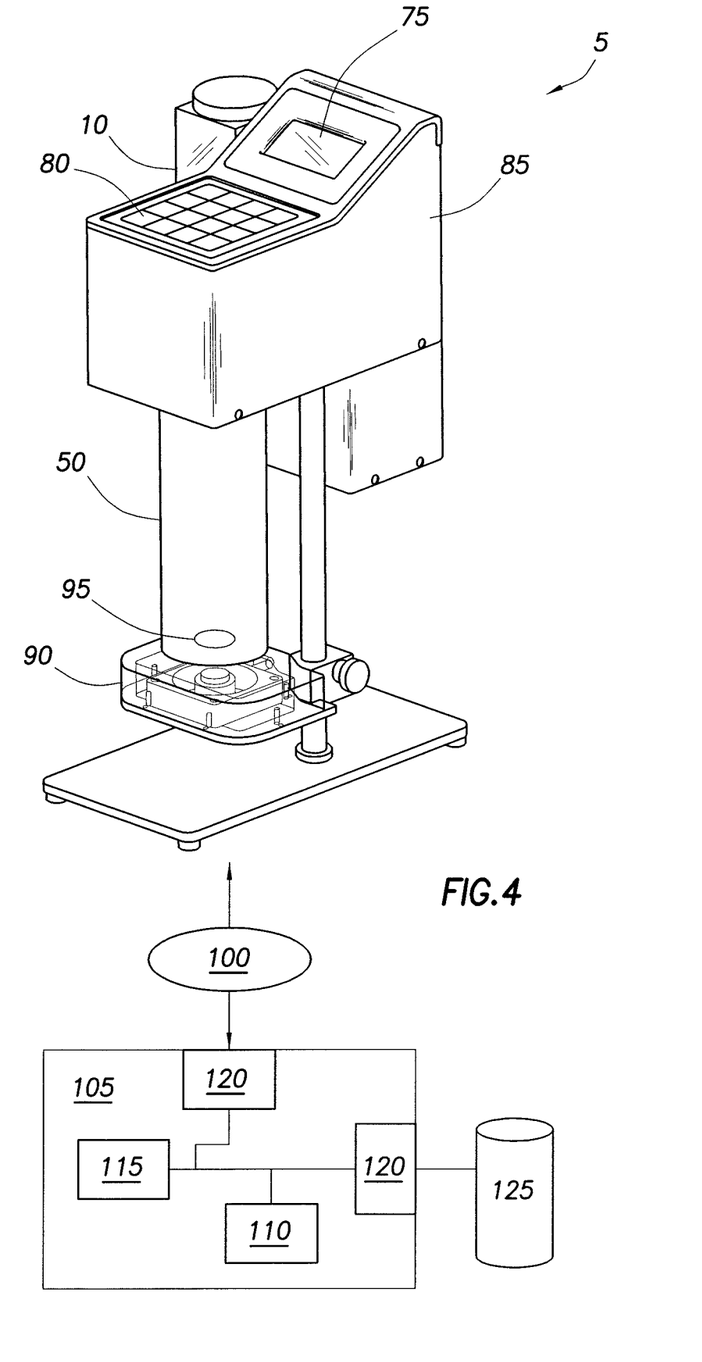
FIG. 4 is an illustration of an example automated calcimeter system with stirring mechanism and communicative coupling to a computer system.

FIG. 4 is an illustration of an example automated calcimeter system 5 with stirring mechanism and communicative coupling to a computer system 105. As illustrated by FIG. 4, automated calcimeter system 5 may comprise reservoir 10, reaction chamber 50, electronics display 75, control pad 80, electronics housing 85, and additionally comprises magnetic plate 90 and magnetic stirrer 95. Magnetic plate 90 and magnetic stirrer 95 may be used to stir the acid-carbonate reaction in reaction chamber 50. Any type of stirring mechanism may be substituted for magnetic plate 90 and magnetic stirrer 95, provided that the substitute mechanism does not undesirably impact the acid-carbonate reaction, for example, by exposing reaction chamber 50 to the external environment.

FIG. 4 additionally illustrates the connection of automated calcimeter system 5 to one example of an external computer system 105 via communication link 100. Communication link 100 may include a direct connection, a private network, a virtual private network, a local area network, a WAN (e.g., an Internet-based communication system), a wireless communication system (e.g., a satellite communication system, telephones), combinations thereof, or any other suitable communication link. Computer system 105 may be any suitable data processing system, including computer systems, handheld devices, or any other suitable device. A suitable data processing system may include processor 110, memory 115, and software operable on processor 110 to process and analyze data generated by automated calcimeter system 5, adjust the parameters of automated calcimeter system 5, and/or operate automated calcimeter system 5. Computer system 105 may comprise a processor 110, memory 115, and input/output ("I/O") interface(s) 120. Processor 110 may comprise one central processing unit or may be distributed across one or more processors in one or more locations. Memory 115 should be communicatively coupled to processor 110. Memory 115 may be read-only memory, random-access memory, or the like. I/O interface(s) 120 should be communicatively coupled to processor 110. I/O interface(s) 120 may be any suitable system for connecting computer system 105 to a communication link, such as a direct connection, a private network, a virtual private network, a local area network, a wide area network ("WAN"), a wireless communication system, or combinations thereof; storage devices, such as storage 125; external devices, such as a keyboard, a monitor, a printer, a voice recognition device, or a mouse; or any other suitable system. Storage 125 may also be provided. Storage 125 may be communicatively coupled to I/O interface(s) 120 or to processor 110. Storage 125 may comprise any device suitable for storing data to be processed, including, but not limited to, compact disc drives, floppy drives, hard disks, flash memory, solid state drives, and the like. Those of ordinary skill in the art will appreciate that suitable data processing systems may comprise additional, fewer, and/or different components than those described for computer system 105.

Figure 5:
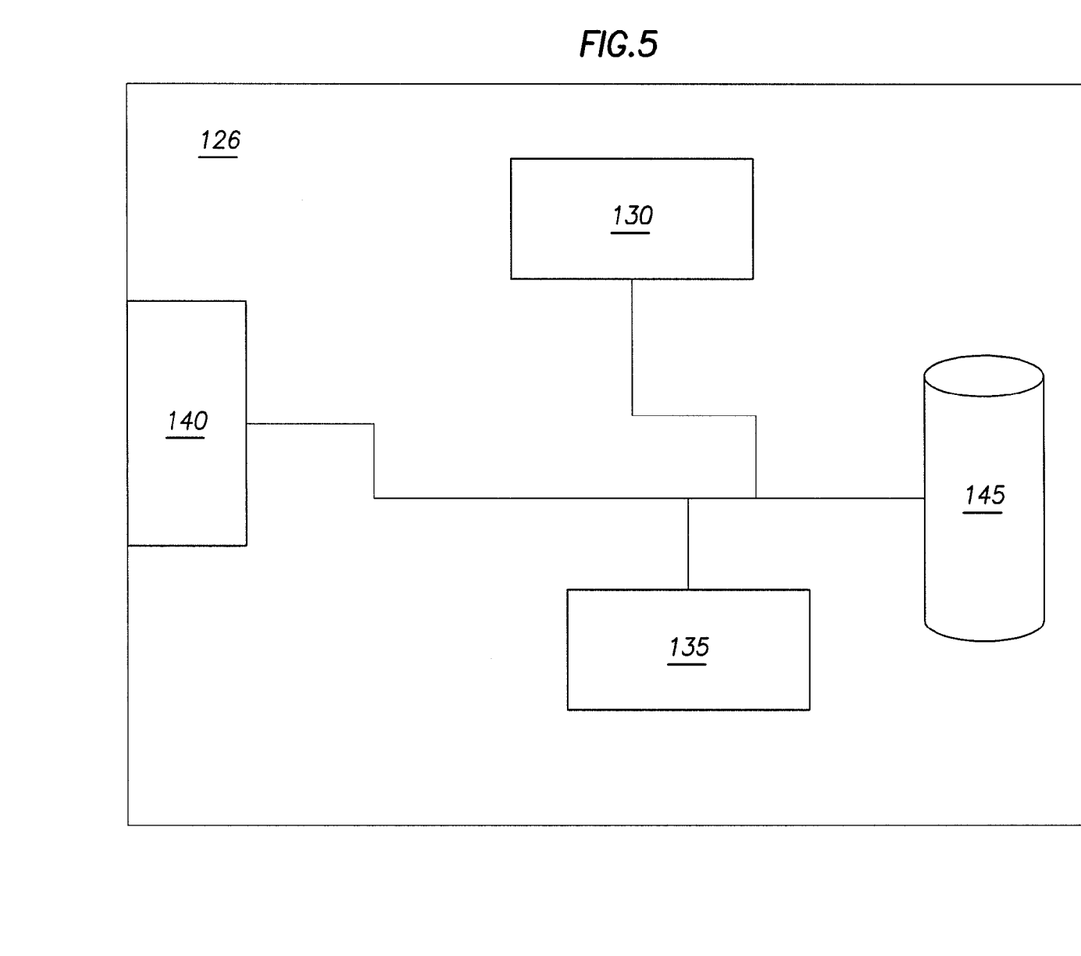
FIG. 5 is an illustration of example internal electronics for an automated calcimeter system.

FIG. 5 illustrates example internal electronic components 126, which may be disposed within and/or about automated calcimeter system 5 and may be used for data processing and analysis, automation, and/or operation of automated calcimeter system 5. As illustrated by FIG. 5, internal electronic components 126 may include calcimeter system processor 130, calcimeter system memory 135, calcimeter system I/O interface(s) 140, and calcimeter system internal storage 145. Additionally, internal electronic components 126 may comprise software operable on calcimeter system processor 130 to process and analyze data generated by automated calcimeter system 5, adjust the parameters of automated calcimeter system 5, automate automated calcimeter system 5, and/or operate automated calcimeter system 5. Calcimeter system processor 130 may comprise one central processing unit or may be distributed across one or more processors in one or more locations. Calcimeter system memory 135 may be communicatively coupled to calcimeter system processor 130. Calcimeter system memory 135 may be read-only memory, random-access memory, or the like. Calcimeter system I/O interface(s) 140 may be communicatively coupled to calcimeter system processor 130. Calcimeter system I/O interface(s) 140 may be any suitable system for automated calcimeter system 5 to a communication link, such as a direct connection, a private network, a virtual private network, a local area network, a wide area network ("WAN"), a wireless communication system, or combinations thereof; external devices, such as an external storage device, a keyboard, a monitor, a printer, a voice recognition device, or a mouse; or any other suitable system. Calcimeter system internal storage 145 may also be provided. Calcimeter system internal storage 145 may be communicatively coupled to calcimeter system processor 130 or calcimeter system I/O interface(s) 140. Calcimeter system internal storage 145 may comprise any device suitable for storing data to be processed, including, but not limited to, compact disc drives, floppy drives, hard disks, flash memory, SSD, and the like. Those of ordinary skill in the art will appreciate that suitable internal electronics and/or data processing systems may comprise additional, fewer, and/or different components than those described for automated calcimeter system 5.

Data processing and analysis software native to automatic calcimeter system 5 and/or internal electronic components 126 and/or installed on computer system 105 may be used to prepare and create a carbonate calibration curve, for example, the software may generate a curve from the measured carbonate content of carbonate standards. Additionally, the data analysis software may be used to analyze the data generated by automated calcimeter system 5 to determine the carbonate content of a sample and the correct treatment for the carbonate in a well operation. As discussed above, the carbonate content measurement of a sample may be obtained through comparison of the carbonate content measurement of a sample with a carbonate calibration curve. Data analysis software native to automatic calcimeter system 5 or installed on computer system 105 may be used to store a calibration curve prepared previously such that samples analyzed later may have their carbon content calculated based on the stored calibration curve. This procedure may be automated such that the analysis happens without the need for operator input or control. Further, the operator may select from several calibration curves and/or sample data prepared and stored previously, thus an operator may be able to recall previously measured and generated calibration curves and samples. Lastly, the data analysis software native to automatic calcimeter system 5 or installed on computer system 105 may be used to measure and compensate for temperature in reaction chamber 50 and provide carbonate content calculations and analysis that compensates for temperature. Any of the data may be transferable and/or storable on a USB drive if desired.

An automated calcimeter system for carbonate content measurement may be provided. The automated calcimeter system may include one or of the components illustrated on illustrated on FIGS. 1-5. The automated calcimeter may include a reaction chamber; a pressure sensor coupled to the reaction chamber and configured to measure pressure in the reaction chamber; a pump coupled to the reaction chamber; piping coupled to the pump, wherein the piping is of sufficient length to store a preselected volume of acid; and a processor configured to instruct the pump to deliver the preselected volume of acid to the reaction chamber while also drawing a volume of gas from the reaction chamber, wherein the volume of gas is equivalent to the preselected volume of acid. The automated calcimeter may further comprise one or more valves coupled to the reaction chamber and coupled to the pump, wherein the one or more valves are configured to direct flow between the pump and the reaction chamber. The automated calcimeter may further comprise a reservoir coupled to the pump. The processor may be further configured to instruct the pump to draw the preselected volume of acid into the piping from the reservoir. The automated calcimeter may further comprise at least two valves, wherein the at least two valves are each coupled to the reaction chamber, the pump, and the reservoir. The valves may have a priming configuration that isolates the reaction chamber from the reservoir while the reservoir is in fluid communication with the pump, and wherein the at least two valves have a reaction configuration that isolates the reservoir from the reaction chamber while the reaction chamber is in fluid communication with the pump. The processor may be further configured to instruct the at least two valves to alternate from the priming configuration to the reaction configuration. The pump may be a peristaltic pump.

A method for carbonate content measurement may be provided. The method may be used in conjunction with one or more of the apparatuses illustrated on FIGS. 1-5. The method may include pumping a volume of acid into a reaction chamber, wherein the acid reacts with a sample in the reaction chamber to produce carbon dioxide and increase pressure in the reaction chamber, wherein the sample comprises a carbonate; drawing gas from the reaction chamber while pumping the volume of acid into the reaction chamber; measuring pressure increase in the reaction chamber; and analyzing the measured pressure increase to determine carbonate content of the sample. The sample may be a ground sample of an oil well core or drill cuttings. The acid may be hydrochloric acid. The carbonate content that may be determined is the content of calcium carbonate or magnesium carbonate. The method may further comprise drawing the volume of acid from a reservoir and storing the volume of acid in piping. Prior to the drawing the volume of acid, the method may further comprise isolating the reaction chamber from the pump using one or move valves while placing the pump in fluid communication with the reservoir. The method may further comprise isolating the reservoir from the pump using the one or more valves while placing the pump in fluid communication with the reaction chamber. The acid may be pumped to the reaction chamber without exposure of the acid to the external environment. A pump coupled to the reaction chamber may be used to pump the volume of acid to the reaction chamber and to draw the g from the reaction chamber. The method may further comprise displaying the measured carbonate content. The method may further comprise storing the measured carbonate content. The method may further comprise a processor instructing a pump to pump the volume of acid to the reaction chamber.

The preceding description provides various embodiments of the automated calcimeter systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

Therefore, the present embodiments are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. An automated calcimeter system comprising:
   a reaction chamber;
   a pressure sensor coupled to the reaction chamber and configured to measure pressure in the reaction chamber;
   a pump coupled to the reaction chamber;
   piping coupled to the pump, wherein the piping is of sufficient length to store a preselected volume of acid; and
   a processor configured to instruct the pump to deliver the preselected volume of acid to the reaction chamber while also drawing a volume of gas from the reaction chamber, wherein the volume of gas is equivalent to the preselected volume of acid.

2. A system according to claim 1, further comprising one or more valves coupled to the reaction chamber and coupled to the pump, wherein the one or more valves are configured to direct flow between the pump and the reaction chamber.

3. A system according to claim 1 further comprising a reservoir coupled to the pump.

4. A system according to claim 3, wherein the processor is further configured to instruct the pump to draw the preselected volume of acid into the piping from the reservoir.

5. A system according to claim 3, further comprising at least two valves, wherein the at least two valves are each coupled to the reaction chamber, the pump, and the reservoir.

6. A system according to claim 5, wherein the at least two valves have a priming configuration that isolates the reaction chamber from the reservoir while the reservoir is in fluid communication with the pump, and wherein the at least two valves have a reaction configuration that isolates the reservoir from the reaction chamber while the reaction chamber is in fluid communication with the pump.

7. A system according to claim 6, wherein the processor is further configured to instruct the at least two valves to alternate from the priming configuration to the reaction configuration.

8. A system according to claim 1, wherein the pump is a peristaltic pump.

9. A method for measuring carbonate content comprising:
pumping a volume of acid into a reaction chamber, wherein the acid reacts with a sample in the reaction chamber to produce carbon dioxide and increase pressure in the reaction chamber, wherein the sample comprises a carbonate;
drawing gas from the reaction chamber while pumping the volume of acid into the reaction chamber;
measuring pressure increase in the reaction chamber; and
analyzing the measured pressure increase to determine carbonate content of the sample.

10. A method according to claim 9, wherein the sample is a ground sample of an oil well core or drill cuttings.

11. A method according to claim 9, wherein the acid is hydrochloric acid.

12. A method according to claim 9, wherein the carbonate content that is determined is content of calcium carbonate or magnesium carbonate.

13. A method according to claim 9, further comprising drawing the volume of acid from a reservoir and storing the volume of acid in piping.

14. A method according to claim 13, further comprising, prior to the drawing the volume of acid, isolating the reaction chamber from the pump using one or move valves while placing the pump in fluid communication with the reservoir.

15. A method according to claim 13, further comprising isolating the reservoir from the pump using the one or more valves while placing the pump in fluid communication with the reaction chamber.

16. A method according to claim 9, wherein the acid is pumped to the reaction chamber without exposure of the acid to the external environment.

17. A method according to claim 9, wherein the pumping the volume of acid to the reaction chamber and the drawing the gas from the reaction chamber use a pump coupled to the reaction chamber.

18. A method according to claim 9, further comprising displaying the measured carbonate content.

19. A method according to claim 9, further comprising storing the measured carbonate content.

20. A method according to claim 9, wherein a processor instructs a pump to pump the volume of acid to the reaction chamber.

* * * * *